United States Patent [19]

Parham

[11] Patent Number: 4,566,480

[45] Date of Patent: Jan. 28, 1986

[54] MEDICAL STOPCOCK VALVE ASSEMBLY

[76] Inventor: Allan M. Parham, 302 Plantation Dr., New Bern, N.C. 28560

[21] Appl. No.: 648,238

[22] PCT Filed: Oct. 28, 1983

[86] PCT No.: PCT/US83/01709

§ 371 Date: Jun. 14, 1984

§ 102(e) Date: Jul. 1, 1984

[87] PCT Pub. No.: WO84/01805

PCT Pub. Date: May 10, 1984

Related U.S. Application Data

[63] Continuation-in-part of Ser. No. 438,410, Nov. 1, 1982, abandoned.

[51] Int. Cl.$^4$ ............................................. A61M 5/00
[52] U.S. Cl. .............................. 137/271; 137/625.47; 128/205.24; 604/32; 604/256
[58] Field of Search ............... 137/271, 625.47; 220/380, 352; 604/256, 248, 249, 250, 32, 33, 34; 128/205.24

[56] References Cited

U.S. PATENT DOCUMENTS

| | | | |
|---|---|---|---|
| 3,774,604 | 11/1973 | Danielson | 251/309 X |
| 3,987,930 | 10/1976 | Funson | 220/352 |
| 4,207,923 | 6/1980 | Giurtino | 137/625.47 |
| 4,219,021 | 8/1980 | Fink | 137/625.41 X |

Primary Examiner—Alan Cohan
Attorney, Agent, or Firm—Shefte, Pinckney & Sawyer

[57] ABSTRACT

An improved medical stopcock valve assembly (10,40,60,80) of the type the valve body (11,111,62) of which has extending fluid-directing tubes (14,16,18,114,116,118,66,68,70,214,216,218) at least some of which have a female Luer lock fitting (30,130,72) adapted to receive a Luer lock cap (32) when not in use, is provided with a blind portion (34,42,44,46,48,52,88,90,92,188,190,192) for receiving and storing a cap (32,132,232) when it is out of use such as during a fluid sampling procedure In one form, the blind portion is formed as a female Luer lock fitting (34',130,54). Alternatively, recessed blind portions (188,190,192) may be provided for receiving and engaging the outer rim (233) of the cap (232) to sealably enclose the entire cap interior to maintain it sterile. In one embodiment, a blind fitting (34) is formed on the valve body (11). In another embodiment, a modified Luer cap (50) having a blind extension (52) thereon is mounted on a Luer fitting (70) of a valve (60) such that the blind extension (52) of the cap (50) can receive and store an out-of-use cap (32). In another embodiment, a cap storage member (84) having plural blind extensions (88,90,92) may be slidably attached to and detached from a valve (80).

37 Claims, 7 Drawing Figures

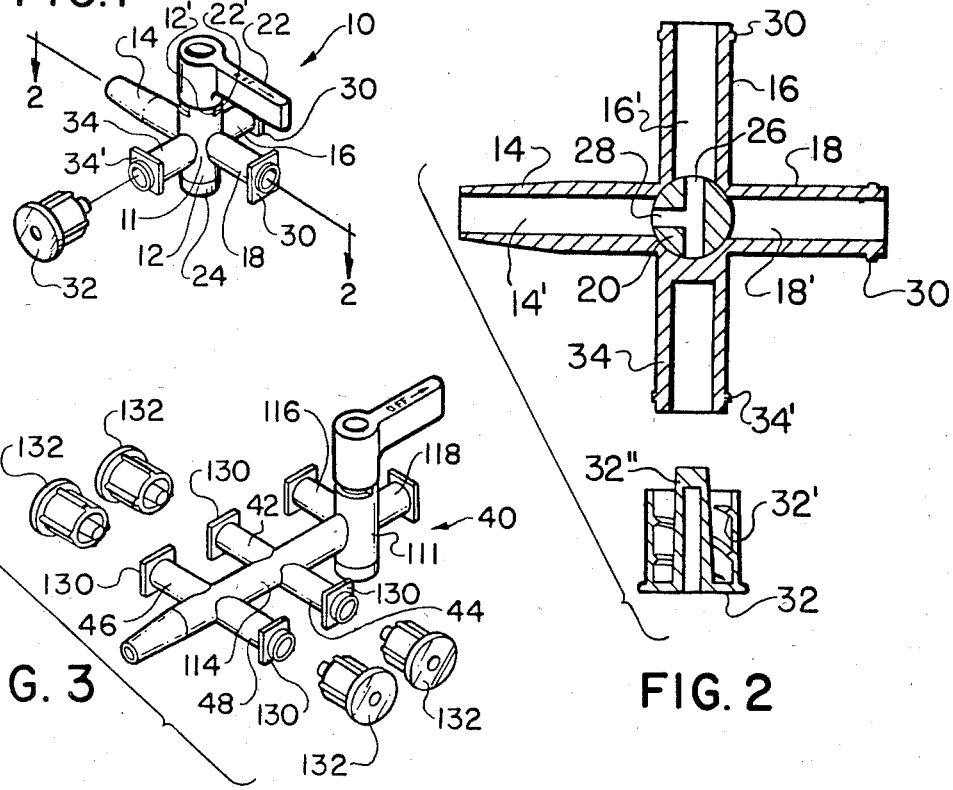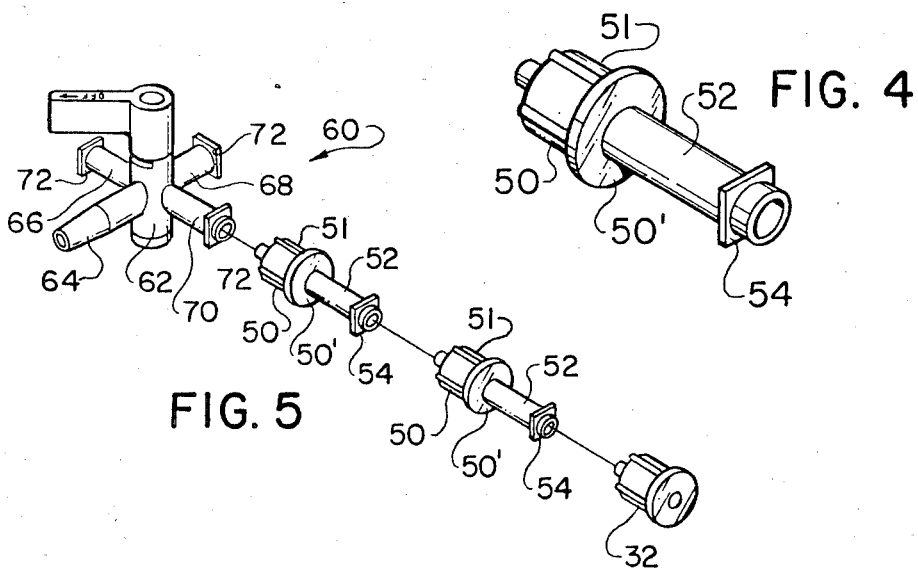

MEDICAL STOPCOCK VALVE ASSEMBLY

CROSS-REFERENCE TO OTHER APPLICATION

This is a continuation in part of co-pending United States patent application Ser. No. 438,410, filed Nov. 1, 1982, now abandoned.

BACKGROUND OF THE INVENTION

The present invention relates to fluid valves and, in particular, to medical stopcock valves.

Small plastic stopcock valve assemblies have long been used routinely in a variety of medical procedures and operations such as, for example, metering the infusion of fluids into the bodies of persons under medical care. Typically, such stopcock valve assemblies include at least a three-way type valve wherein the valve body has three or more radially-arranged ports, and an interior directional control member is rotatably arranged within the valve body for selectively closing one or more ports while opening communication between at least two other ports. Examples of this type of valve are disclosed in U.S. Pat. Nos. 3,185,179; 3,834,372 and 4,207,923.

As will of course be understood, the maintenance of sterile conditions in such uses of these valves is exceedingly important. Accordingly, when one of the valve ports is closed and out of use, a cap or other similar closure device is ordinarily fitted in the valve port to prevent possible entrance therethrough of bacteria, germs or the like into the valve body. In the typical use of such valves, it is often desirable or necessary to alter the operational disposition of the valve to bring into operation the out-of-use port which of course requires the removal of the cap therefrom. For example, in infusion usage of such a valve, it is routine procedure to periodically sample and test the infusion fluid flowing through the valve and/or the body fluid to maintain close control thereof, this being readily accomplished by removing the cap from the out-of-use port and rotating the directional control member to divert a small quantity of the infusion fluid or to withdraw a small quantity of the body fluid through the out-of-use port. Ordinarily any such procedure requires the attendant performing it to use both hands necessitating the cap be placed aside and, in practice, the cap, which is normally very small, is sometimes lost or temporarily misplaced, all of which can create particular problems when the valve is to be returned to its original operational disposition and the cap is to be replaced. As will be understood, the mere setting aside of the cap in itself can jeopardize the sterility thereof and of the valve upon replacement of the cap and, if the procedure requires any significant amount of time to complete, it is ordinary practice to discard the removed caps and to replace it with a new cap when the valve is returned to its original operating state. However, additionally, the loss or misplacement of the cap neessitates that the valve, upon return to its original operating state, be operated at least temporarily without a cap on the out-of-use port until the lost or misplaced cap is located or a replacement cap is obtained, which poses a more significant problem in maintaining the desired sterile condition of the valve.

The present invention provides a significant improvement over the above-described conventional stopcocks by providing a blind accessory member on the valve adapted to receive and store one or more caps when out of use to prevent loss thereof and provide ready access thereto for use when desired.

SUMMARY OF THE INVENTION

The present invention provides an improvement in medical stopcock valve assemblies of the type including a valve body having formed therein a plurality of fluid ports, an operating member in the valve body for selectively controlling fluid communication through the valve body between the fluid ports, and at least one closure member having an engagement arrangement formed for selective engagement with the valve body at at least one of the fluid ports for closure thereof. Briefly described, the improvement includes a blind portion on the valve assembly out of operative communication with the fluid ports and formed for engagement by a closure device to receive and retain it for storage when not in port-closing use.

Preferably, the valve is of the type the ports of which are formed as tubes projecting from the valve body with at least one of which tubes having a tubular female fitting and the closure device being a cap having a projecting male engaging portion selectively engagable in the female fitting. It is contemplated that the blind portion may be formed either on the valve body, on a modified form of cap, or on a specially formed cap storage member attachable to the valve body and further that the blind portion may be of the same form as an operative female fitting of the valve or may be of a modified form adapted to sealably enclose the interior port-closing engagement portions of the stored cap. It is also contemplated that plural blind portions may be provided for storage of plural caps.

In one embodiment of the present invention, the valve is at least a threeway type stopcock valve having at least three fluid-directing tubes at least one of which has a female fitting, the blind portion in this embodiment being formed on the valve body preferably as a blind accessory tube closed to operative communication interiorly thereof and having a tubular female fitting identical to the fitting of the fluid directing tube formed for engagement by the cap for storage thereof.

In another embodiment of the present invention, the valve is at least a four-way type stopcock valve having at least four fluid-directing tubes at least two of which have a tubular female fitting. In this embodiment, a modified cap is utilized having a conventional male engaging portion for selective engagement in a female fitting, on which cap a blind cap-receiving portion is formed as a tubular female fitting to receive and retain for storage another cap, the modified cap being selectively engagable with one of the female fittings of the fluid directing tubes and the blind fitting of the improved cap being engagable by the conventional cap for storage thereof.

In a third embodiment, the valve is at least a three-way stopcock valve of the above-described type and a separate cap storage member is provided having plural blind portions adapted for stored engagement of plural caps. One of the tubes of the valve and the cap storage member are formed with mating elements permitting sliding receipt of the cap storage member on the tube for ready access to its caps for use and permitting sliding removal of the cap storage member from the tube following use of the stored caps for replenishment of the cap storage member with other caps or for replacement by another cap storage member having other caps stored thereon.

BRIEF DESCRIPTION OF THE DRAWINGS

FIG. 1 is a perspective view of a medical stopcock valve assembly according to the preferred embodiment of the present invention;

FIG. 2 is a horizontal cross-sectional view thereof taken along line 2—2 of FIG. 1;

FIG. 3 is a perspective view of a modified form of medical stopcock valve assembly according to another embodiment of the present invention;

FIG. 4 is a perspective view of a modified form of cap according to another embodiment of the present invention;

FIG. 5 is a perspective view of a medical stopcock valve assembly employing the modified cap of FIG. 4;

DESCRIPTION OF THE PREFERRED EMBODIMENT

Figure 6:
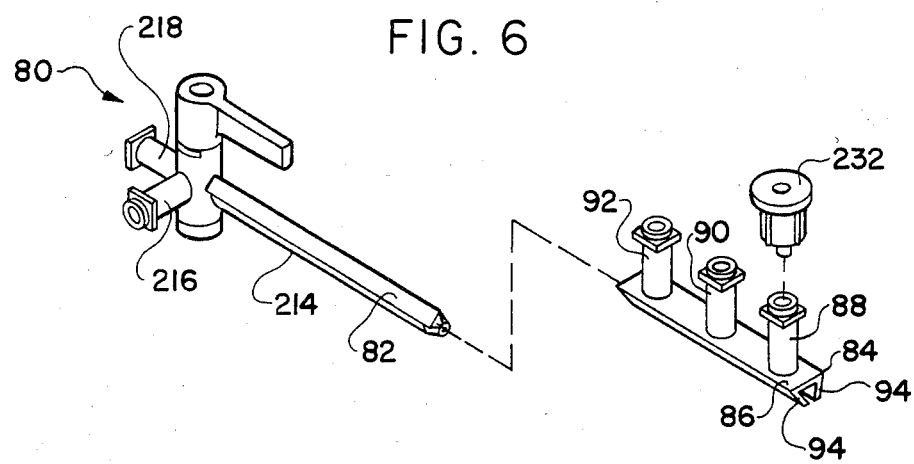
FIG. 6 is a perspective view of a modified form of medical stopcock valve assembly according to another embodiment of the present invention.

Referring now to the accompanying drawings and initially to FIGS. 1 and 2, one preferred embodiment of the stopcock valve assembly of the present invention is indicated generally at 10. The valve assembly 10 includes a stopcock valve 11 having a cylindrical valve body 12 from which tubular extensions 14,16,18 radially extend coplanarly at ninety degree spacings. The valve body 12 is hollow and each tubular extension 14,16,18 opens thereinto through a respective fluid port 14',16',18' in the valve body 12 for fluid communication between the tubular extensions 14, 16, 18 through the hollow interior of the valve body 12. A cylindrical core 20 of greater axial extent than the valve body 12 is rotatably fitted snugly in the valve body 12 with a portion of the core 20 extending upwardly from the upper edge of the valve body 12 and another portion of the core 20 extending downwardly from the lower edge of the valve body 12. A handle 22 is rigidly affixed to the upwardly extending core portion for actuating rotational movement of the core 20 within the valve body 12. The lowermost end of the core 20 has affixed thereto a cylindrical retaining member 24 of approximately the same diameter as the valve body 12. The core 20 has a bore 26 formed diametrically therethrough and another bore 28 formed radially therethrough perpendicularly to and opening into the bore 26, the bores 26,28 being thusly formed at a selected disposition axially along the core 20 to be in the same plane as the ports 14',16',18' and tubular extensions 14,16,18 in the assembled form of the valve 11 to provide for selective communication between any two of the tubular extensions 14,16,18 by selective rotational positioning of the core 20 within the valve body 12. For convenience of operation, the handle 22 is affixed to the core 20 to extend radially oppositely of the bore 28 whereby in any operative position of the core 20 the handle 22 extends in the direction of the tubular extension 14,16, or 18 which is closed by the core 20 in the respective operative position and cooperating shoulders 12',22' are formed on the valve body 12 and the handle 22 as stop surfaces for accurate positioning of the handle 22. The tubular extension 14 is tapered in the form of a male taper so as to be adapted to fit into the female taper of a hypodermic needle hub (not shown) or to be connected to conventional flexible tubing (not shown). Each of the tubular extensions 16,18 are formed at their respective extending ends with a hollow female fitting 30 in the form of a femal Luer lock fitting having an outward annular flange, capable of receiving and engaging a mating cap 32 of the Luer lock type with the projecting male engaging portion 32'' of the cap 32 engaged in the tubular fitting 30 and the interior threads 32' of the cap 32 threadedly engaging the flange of the fitting 30, or alternatively capable of receiving conventional flexible tubing (not shown).

As will be understood, the stopcock assembly 10 as thus far described is of the conventional type described and illustrated in the aforesaid U.S. Pat. Nos. 3,185,179 and 4,207,923 to which reference may be had for a more complete specification thereof. According to the first embodiment of the present invention, another tubular extension 34 is formed on and extends outwardly from the valve body 12 coplanarly with the tubular extensions 14,16,18 intermediate the tubular extensions 14,18 but is inwardly closed to communication with the hollow interior of the valve body 12 and therefore is inoperative for fluid communication through the valve body 12 with the ports 14',16',18' and tubes 14,16,18, the tubular extension 34 having formed thereon at its outward end a hollow flanged female Luer lock fitting 34' identical to the Luer fittings 30 whereby the tubular extension 34 constitutes in effect a blind extension for the accessory purpose of inserting therein and threadedly mounting thereon a Luer lock cap 32 for storage thereof when not in port-closing use on one of the tubular extensions 16,18 and to provide ready access to the stored cap 32 for engagement on one of the tubular extensions 16,18 when desired. Thus, a cap 32 may be conveniently stored for ready use in a manner shielding the male projecting portion 32'' and the interior threads 32' of the cap 32 to best insure the sterility thereof. It is contemplated that ordinarily the blind tubular extension 34 will be provided with a cap 32 of its own in setting up the valve 11 of use whereby the stored cap 32 will be readily accessible for use when or if necessary such as for replacement of a cap 32 removed from one of the tubular extensions 16,18 during a lengthy sampling or similar procedure or for quick replacement of a removed cap 32 which has been lost or misplaced. As will be understood, the caps 32 are inexpensive and are considered disposable and therefore such above-described use of the blind tubular extension 34 is considered preferable insofar as insuring and best maintaining sterile conditions. Alternatively, the blind tubular extension 34 may be employed for temporarily mounting thereon for storage a cap 32 during removal thereof from one of the tubular extensions 16,18 to provide ready access to the cap 32 for its replacement on the tubular extension 16,18 when desired.

For example, in the infusion of blood or other fluids into the human body, stopcock assemblies 10 of the present type are routinely employed as a metering valve in the flexible tubing used in such a procedure. As will be understood, the stopcock 10 is typically arranged with the tubular extension 18 acting as an inlet conduit communicating through a length of tubing (not shown) with the fluid source, with the tubular extension 14 acting as an outlet conduit communicating through another length of tubing (not shown) with the patient, and with the core 20 positioned to align the bore 26 with the tubular extensions 14,18 for communication therebetween, the tubular extension 16 thereby being closed and out of operation and the Luer lock cap 32 being fitted thereover. In this conventional infusion procedure, it is an ordinary control procedure to periodically divert a small quantity of the infusion fluid for testing as well to periodically withdraw from the patient a small quantity of body fluid for testing, this being done when desired by removing the Luer lock cap 32 from the tubular extension 16 and operating the stopcock handle 22 to provide communication between the tubular extension 16 and the tubular extension 18, in the first instance, and alternatively the tubular extension 14, in the second instance. In either case, the operation generally requires the attendant performing the procedure to use both hands and further may take several minutes to complete. As above mentioned, with conventional stopcocks, the Luer lock cap 32 must accordingly be set aside and is often misplaced temporarily or lost altogether. Since it is important to maintain sterile conditions, it is highly desirable to complete such a fluid sampling operation as quickly as possible and to minimize the time period during which the Luer lock cap 32 is removed from the tubular extension 16. Merely setting aside the cap 32 creates a possibility that it may be contaminated by bacteria, germs and the like and furthermore any misplacement, however temporary, or loss of the cap 32 greatly increases the chances of the introduction of bacteria, germs or the like into the stopcock 10 through the tubular extension 16. The provision in the present stopcock 10 of the blind tubular extension 34 eliminates these dangers by providing a convenient, non-interfering mated fitting on which a Luer lock cap 32 may be received and retained for storage thereof to provide ready access to the stored cap 32 when need such as in a sampling or similar procedure of the above-described type. Once the procedure is completed, the cap 32 may be readily accessed for placement on the tubular extension 16. Thus, the storage of the cap 32 on the blind fitting 34 not only tends to maintain the cap 32 more sterile than if it were merely placed aside, but also helps to minimize any chance that germs, bacteria or the like may enter the valve 11 through the tubular extension 16.

Those skilled in the art will understand that the present invention is susceptible of a broad utility not limited to the above-described specific embodiment and particularly that the blind tubular extension 34 need not necessarily be formed at the described location on the valve body 12. Thus, the tubular extension 34 may for instance be formed on one of the tubular extensions 14,16,18, or on the retaining member 24 to extend downwardly therefrom, or on the handle 22 at its axis to extend upwardly therefrom. Furthermore, the blind tubular extension 34 may readily be embodied in types of medical stopcocks or valves other than the three-way type stopcock valve 11 and, if desirable, more than one blind tubular extension 34 may be provided. Additionally, it will be understood that the present invention is not limited in application to stopcock valves employing Luer-type lock caps 32 and female Luer-type lock fittings nor is it critical that the blind tubular extension 34 be formed with a female fitting of the Luer lock type 34', but instead the present invention may be readily adapted in any type stopcock valve employing a closure device on a mating out-of-use port and the blind tubular extension may accordingly be formed with any type fitting appropriate to accommodate the closure device in use. For instance, various types of conventional caps or other closure devices other than a Luer lock cap 32 may be employed in the particular embodiment of FIG. 1, such as a plain, non-threaded cap having no male projecting portion, and, similarly, various types of conventional female fittings other than the flanged-type Luer lock fitting 34' which are also adapted to receive a Luer lock cap 32 or other cap or closure device may be employed in the particular embodiment of FIG. 1, such as a threaded screw-type, non-flanged fitting or a simply non-flanged, non threaded cylindrical tubular extension both of which are equally capable of receiving and retaining a Luer lock cap 32. It is also contemplated that the blind portion or member may be constructed to substantially or entirely enclose sealably the interior of the stored Luer lock or other cap or to otherwise seal the valve engaging, port closing surfaces and portions of the closure device being employed thereby to maintain the stored cap or other closure device in a sterile condition prior to use thereof. Thus, for example, the blind portion may be formed to engage sealably the outer rim of the Luer lock cap 32. In addition, the blind tubular extension or extensions or the other blind portion or portions may be constructed to be readily attachable and detachable from the valve body 12 for ready replacement of the blind portion or portions and one or more caps or closure devices carried thereby as a unit following use of caps or closure devices stored thereon.

One modified form of stopcock assembly is shown in FIG. 3 at 40 and basically includes a stopcock valve portion 111 of the same three-way construction as the stopcock 11 having flanged tubular extensions 114,116,118 with its tubular extension 114 being substantially elongated and having formed therealong four blind accessory tubular extensions 42,44,46,48 each being closed from operative communication with the interior of the tubulr extension 114 and each having a hollow flanged female Luer lock fitting 130 at its respective extending end for threadedly receiving and storing a respective Luer lock cap 132. For convenience and flexibility of use of this form of the present invention with conventional stopcocks 11, it is contemplated that the elongated portion of tubular extension 114 may be constructed as a separate individual item adapted for assembled engagement with the male Luer taper of the tubular extension of a conventional stopcock 11 to form the valve assembly 40. Those skilled in the art will appreciate that blind tubular extensions according to the present invention may be equally well embodied in other forms of attachments adapted for engagement on conventional stopcock valves to facilitate storage of one or more Luer lock caps 32, such as, for example, a clip-type device formed to be friction snap-fitted on the valve body and having one or more female fittings 34 formed thereon for receiving caps 32.

FIG. 4 illustrates another embodiment of the present invention in a modified form of a Luer lock cap, indicated generally at 50. According to this embodiment, the Luer lock cap 50 is formed with a cap portion 51 of the conventional construction of the caps 32,132 having a cylindrical portion with a projecting male engaging portion and with interiorly formed threads (not shown) adapted for insertion in and to threadedly engage the flanges of a conventional female Luer lock fitting (e.g. 30,130, FIGS. 1, 2, 4). Affixed to and extending outwardly from the flat radial surface 50' of the cap 50 is a blind tubular extension 52 inwardly closed from communication through the cap 50 which extension 52 has a hollow flanged end portion 54 of the form of a conventional female Luer lock fitting adapted to threadedly receive either a conventional Luer lock cap 32 or the cap portion 51 of another modified cap 50. In this manner, the Luer lock cap 50 provides substantial flexibility in the application and use of the present invention in that, employing the Luer lock cap 50, certain conventional stopcocks may be readily adapted to practice the present invention by merely mounting the Luer lock cap 50 on a non-operating tubular extension thereof and alternatively the Luer lock cap 50 may be mounted on the blind tubular extension of a stopcock 11 or 40 of the present invention and plural additional Luer lock caps 50 and/or a conventional cap 32 may be stacked on the first cap 50 (FIG. 5) to increase the cap storage capacity of the stopcocks 11,40.

More specifically, in the first above-described instance of use of the Luer lock cap 50, any conventional medical stopcock valve of at least a four-way or greater capability having four or more tubular extensions at least two of which have female Luer lock fittings may be readily adapted for use in the above-described three-way manner of the stopcocks 11,40 or in any similar manner. As seen in FIG. 5, a conventional stopcock valve of the four-way type is generally indicated at 60 and includes a valve body 62 having four fluid directing ports formed as tubular extensions 64,66,68,70 from the valve body 62 and an appropriate interior control member (not shown) disposed in the valve body 62 to control selectively communication between the four ports. Each of the three tubular extensions 66,68,70 are formed at their outer ends with a flanged female Luer lock fitting 72 adapted conventionally to receive a Luer lock cap. The various modes of operation of the valve 60 are well known and need not be described herein, but reference may be made to U.S. Pat. No. 3,834,372 for a disclosure of one exemplary such valve 60. As will be understood, the valve 60 may be employed in either a two-way, three-way or four-way manner as desired and, in using it in a three-way manner, only three of the fluid-directing tubular extensions, e.g. 64,66,68, will be needed for operation and the other tubular extension 70 will be out of operation throughout the use of the valve 60. Accordingly, in such a use of the valve 60, the modified Luer lock cap 50 may be mounted on the fitting of the out-of-use tubular extension 70 to permit the stacked storage of plural modified Luer lock caps 50 as shown in FIG. 5. As those skilled in the art will recognize, such a use of the modified Luer lock cap 50 to adapt conventional valves to the present invention will find greatest practical application in valves of greater than four-way capacity wherein only one tubular extension may not be needed for operation but the capacity for storage of several Luer lock caps at one time may be required. The particular embodiment of the present invention shown in FIG. 5 is therefore considered to be illustrative of such a use of the cap 50 of the present invention and not to limit the scope thereof.

FIG. 6 illustrates another modified form of three-way stopcock valve assembly indicated generally at 80 having tubular extensions 214,216,218 the tubular extension 214 of which is substantially elongated and on the exterior of which is formed a longitudinally extending track 82 of an inverted triangular shape. A cap storage member 84 capable of receiving and storing several Luer lock caps 232 is provided for selective attachment to and detachment from the track 82, the cap storage member 84 having a substantially flat platform 86 from one surface of which extend three blind accessory tubular extensions 88,90,92 of female Luer lock construction adapted to receive three Luer lock caps 232 and from the longitudinal side edges of which respective flanges 94 extend convergingly in the opposite direction from the extensions 88,90,92 at angles compatible with the track 82 for sliding attachment thereon and removal therefrom. It will thus be understood that the cap storage member 84 with three caps 232 stored thereon may be attached as a unit to the tubular extension 214 to provide ready access to the caps 232 for use as needed and then may be readily removed following usage of each of the caps 232 for ready replacement with another fully stocked cap storage member 84 and for replenishment of the original cap storage member 84 with fresh sterile caps. In this manner, a sufficient supply of caps 232 may always be maintained readily available for use with minimal time being necessary for replacing used caps 232 with fresh stored caps 232.

Figure 7:
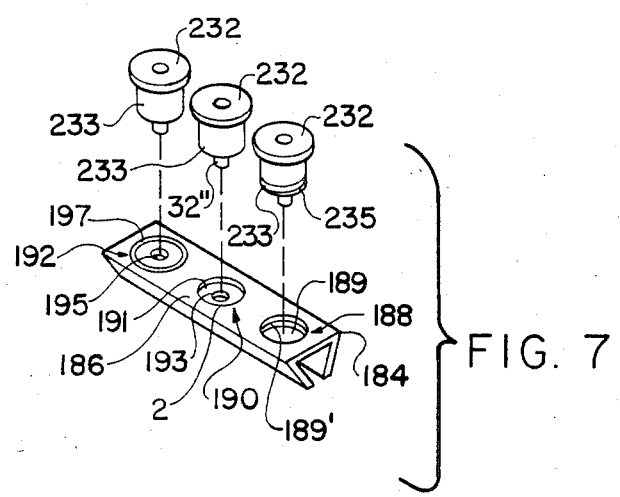
FIG. 7 is a perspective view of a cap storage member of the type of FIG. 6 illustrating three alternate arrangements for stored mounting of caps according to further embodiments of the present invention.

Another cap storage member 184 of the type of cap storage member 84 is illustrated in FIG. 7 and is provided with three alternate arrangements for securing mounting of the caps 232 in a totally sealed manner, indicated generally at 188,190,192. As will be understood, the several cap mounting arrangements in any one cap storage member of this type will ordinarily be of the same construction, the cap storage member 184 having three differing forms of cap mounting arrangement solely for purposes of illustration. With the conventional male-female Luer lock mounting of the foregoing described constructions, substantially only the projecting male engaging portion 32" is sealably shielded during storage and therefore some risk exists that the remaining interior surfaces of the cap such as the interior threads 32' may become contaminated during storage of the cap and may transmit the contamination to the valve upon later use of the stored cap. The cap mounting arrangements 188,190,192 substantially eliminate this risk by sealably engaging in alternate manners the outer rim 233 of a stored cap 232 thereby entirely enclosing and shielding the interior of the cap 232 to maintain its sterile. More specifically, the cap mounting arrangement 188 provides a cylindrical recess 189 in the platform 186 of the cap storage member 184 the side wall of which recess 189 is threaded at 189' to be adapted for sealed threaded engagement with compatible threads 235 specially formed exteriorly on a modified cap 232 adjacent its outer rim 233. The cap mounting arrangement 190 provides a first cylindrical recess 191 adapted to receive the outer rim 233 of a cap 232 by a relatively close sealed friction fit with a further central recess 193 therein adapted to receive the projecting male engaging portion 32". The cap mounting arrangement 192 provides only a small central recess 195 adapted to receive the male engaging portion 32" of a cap 232 and has a circular adhesive gasket 197 on the surface of the platform 186 for sealing engagement of the outer rim 233 of the cap 232.

Those persons skilled in the art will readily recognize that other cap mounting arrangements are equally adaptable for sealed engagement with the outer rim of a stored cap within the scope of the present invention. For instance, the outer cap rim and the blind portion may be compatibly tapered to frictionally fit together in a substantially similar manner to the tapered engagement between the male engaging portion and female receiving portion of a conventional Luer lock system.

The present invention has been described in detail above for purposes of illustration only and is not intended to be limited by this description or otherwise to exclude any variation or equivalent arrangement that would be apparent from, or reasonably suggested by the foregoing disclosure to the skill of the art.

The embodiments of the invention in which an enclusive property or privilege is claimed are defined as follows:

1. In a medical stopcock valve assembly of the type including a valve body having formed therein a plurality of fluid ports, an operating member in said valve body for selectively controlling fluid communication through said valve body between said fluid ports, and at least one closure means having engagement means formed for selective engagement with said valve body at at least one of said fluid ports for closure thereof, the improvement comprising blind closure-receiving means formed integrally on said valve body closed to operative communication with said fluid ports and formed for engagement by a stored closure means having engagement means identical to said at least one closure means to receive and retain said stored closure means for storage thereof when not in portclosing use to prevent loss thereof and to provide ready access thereto for portclosing use when desired.

2. The improvement in a medical stopcock valve assembly according to claim 1 and characterized further in that said at least one closure means constitutes said stored closure means to be received and retained on said blind closure-receiving means.

3. The improvement in a medical stopcock valve assembly according to claim 1 and characterized further in that said stored closure means comprises a cap, said engagement means thereof including a projecting male engaging portion formed thereon for engagement in a mating female member, and said blind closure-receiving means is formed as a tubular female fitting formed integrally on said valve body and adapted for mating receiving engagement with said projecting portion of said stored closure means.

4. The improvement in a medical stopcock valve assembly according to claim 1 and characterized further by plural said blind closure-receiving means on said valve assembly for receiving and retaining plural said stored closure means for ready access to each thereof for use.

5. In a medical stopcock valve assembly of the type including a valve body having formed therein a plurality of fluid ports, an operating member in said valve body for selectively controlling fluid communication through said valve body between said fluid ports, and at least one closure means having engagement means formed for selctive engagement with said valve body at at least one of said fluid ports for closure thereof, the improvement comprising a unit having plural blind closure-receiving means each formed for engagement by plural stored closure means having engagement means identical to said at least one closure means to receive and retain said stored closure means for storage thereof when not in port closing use to prevent loss thereof and to provide ready access thereto for portclosing use when desired, and mated affixation means on said unit and said valve body for removable affixation of said unit to said valve body for ready removal following use of said plural stored closure means and replacement thereof with another unit of plural blind closure-receiving means carrying plural stored closure means for use thereof.

6. The improvement in a medical stopcock valve assembly according to claim 5 and characterized further in that said affixation means is adapted for slidable receipt of said unit on and removal of said unit from said valve body.

7. The improvement in a medical stopcock valve assembly according to claim 1 and characterized further in that said blind closure-receiving means is adapted for sealing said engagement means of said stored closure means for maintaining said engagement means sterile.

8. In a medical stopcock valve assembly including an at least three-way-type stopcock valve having a hollow valve body having at least three fluid-directing tubes communicating interiorly with and projecting from said valve body, each of at least one of said tubes having a tubular female fitting, a valve operating member movably disposed interiorly of said valve body for selective movement to control fluid communication through said valve body between said fluid directing tubes, and cap means having a projecting male engaging portion formed thereon for selective engagement in the tubular female fitting for closure of its said fluid-directing tube, the improvement comprising a blind accessory tube formed integrally on said valve body closed to operative communication interiorly with said valve body and said tubes and including a female fitting formed for mated receiving engagement of said projecting portion of said cap means for receiving and retaining it for storage thereof when not in tube-closing use to prevent loss thereof and to provide ready access thereto for tube-closing use when desired.

9. In a medical stopcock valve assembly including an at least three-way-type stopcock valve having a hollow valve body having at least three fluid-directing tubes communicating interiorly with and projecting from said valve body, each of at least one of said tubes having a tubular female fitting, a valve operating member movably disposed interiorly of said valve body for selective movement to control fluid communication through said valve body between said fluid directing tubes, and cap means having a projecting male engaging portion formed thereon for selective engagement in the tubular female fitting for closure of its said fluid-directing tube, the improvement comprising a cap storage member having formed thereon plural blind cap-receiving means formed for engagement by plural stored cap means having male engaging portions identical to said cap means for receiving and retaining them for storage thereof when not in tube-closing use to prevent loss thereof and mated affixation means on said cap storage member and exteriorly on one said tube for detachable receipt of said cap storage member on said one tube for ready access to said stored cap means for tube-closing use when desired and for ready removal of said cap storage member from said one tube following use of said stored cap means for replenishment with other cap means or replacement by another cap storage member with other cap means.

10. A fluid conveying member for use in a medical fluid flow system or the like comprising a tubular portion having a fluid-conveying passageway therethrough, said tubular portion having connection means at the ends of its said fluid-conveying passageway for engagement with other fluid conveying members in fluid communication therewith, at least one closure means of the type having engagement means formed for selective port-closing engagement with a medical stopcock valve assembly, and at least one blind closure-receiving portion formed integrally on said tubular portion out of operative communication with said fluid passageway and having a portion formed for engagement by a stored closure means having engagement means identical to said at least one closure means to receive and retain said stored closure means for storage thereof when not in port-closing use to prevent loss thereof and to provide ready access thereto for tube-closing use when desired.

11. A fluid conveying member for use in a medical fluid flow system according to claim 10 and characterized further in that said stored closure means comprises a cap, said engagement means thereof including a projecting male engaging portion formed thereon for engagement in a mating female member, and said portion of said blind member is formed as a tubular female fitting adapted for mating receiving engagement with said projecting portion of said stored closure means.

12. A fluid conveying member for use in a medical fluid flow system or the like comprising a tubular portion having a fluid-conveying passageway therethrough, said tubular portion having connection means at the ends of its said fluid-conveying passageway for engagement with other fluid conveying members in fluid communication therewith, at least one closure means of the type having engagement means formed for selective port-closing engagement with a medical stopcock valve assembly, and a closure storage member on said tubular portion, said closure storage member having plural blind closure-receiving portions formed thereon out of operative communication with said fluid passageway and having respective portions formed for engagement by plural stored closure means having respective engagement means identical to said at least one closure means for receiving and retaining said plural stored closure means for storage thereof when not in port-closing use to prevent loss thereof and to provide ready access thereto for port-closing use when desired, said closure storage member and said tubular portion having mated affixation means formed thereon for sliding receipt of said closure storage member on said tubular portion for ready access to said plural stored closure means for port closing use and for ready sliding removal of said closure storage member from said tubular portion following use of said stored closure means for replenishment with other closure means or replacement by another closure storage member with other closure means stored thereon.

13. A fluid conveying member for use in a medical fluid flow system according to claim 10 and characterized further in that said blind closure-receiving means is adapted for sealing said engagement means of said stored closure means for maintaining said engagement means sterile.

14. A fluid conveying member for use in a mdical fluid flow system according to claim 13 and characterized further in that said stored closure means comprises a cap, said engagement means thereof including screw thread means formed internally of said cap and a projecting male engaging portion extending interiorly within said cap, said blind closure-receiving means being adapted to sealably enclose the interior of said cap upon engagement therewith.

15. The improvement in a medical stopcock valve assembly according to claim 7 and characterized further in that said stored closure means comprises a cap having an outer rim and having said engagement means formed interiorly, said blind closure-receiving means including means for sealably engaging said rim.

16. The improvement in a medical stopcock valve assembly according to claim 15 and characterized further in that said sealably engaging means includes means for frictionally engaging snugly said rim.

17. The improvement in a medical stopcock valve assembly according to claim 16 and characterized further in that said rim and said frictionally engaging means respectively have mating tapered surfaces for engagement therebetween.

18. The improvement in a medical stopcock valve assembly according to claim 17 and characterized further in that said engagement means of said stored closure means includes screw thread means formed internally of said cap and a projecting male engaging portion extending interiorly within said cap, said blind closure-receiving means being adapted to sealably enclose the interior of said cap upon engagement therewith.

19. The improvement in a medical stopcock valve assembly according to claim 9 and characterized further in that each said stored cap means has an outer rim and has said male engaging portion formed interiorly, each said blind cap-receiving means including means for sealably engaging the rim of one said stored cap means.

20. The improvement in a medical stopcock valve assembly according to claim 19 and characterized further in that said sealably engaging means includes means for frictionally engaging snugly said rim.

21. The improvement in a medical stopcock valve assembly according to claim 20 and characterized further in that said rim and said frictionally engaging means respectively have mating tapered surfaces for engagement therebetween.

22. The improvement in a medical stopcock valve assembly according to claim 21 and characterized further in that said mated affixation means provides sliding receipt and removal of said cap storage member on and off said one tube.

23. A fluid conveying member for use in a medical fluid flow system according to claim 10 and characterized further in that said stored closure means comprises a cap having an outer rim and having said engagement means formed interiorly, said blind closure-receiving member including means for sealably engaging said rim.

24. A fluid conveying member for use in a medical fluid flow system according to claim 23 and characterized further in that said sealably engaging means includes means for frictionally engaging snugly said rim.

25. A fluid conveying member for use in a medical fluid flow system according to claim 24 and characterized further in that said rim and said frictionally engaging means respectively have mating tapered surfaces for engagement therebetween.

26. A fluid conveying member for use in a medical fluid flow system according to claim 12 and characterized further in that said stored closure means comprise plural caps, each said engagement means thereof including a projecting male engaging portion formed thereon for engagement in a mating female member, and said blind portions are formed as tubular female fittings adapted for mating receiving engagement with said projecting portions of said stored closure means.

27. A fluid conveying member for use in a medical fluid flow system according to claim 12 and characterized further in that said blind closure-receiving portions are adapted for sealing said engagement means of said stored closure means.

28. A fluid conveying member according to claim 27 and characterized further in that each said stored closure means comprises a cap having an outer rim and having said engagement means formed interiorly, each said blind closure-receiving portion including means for sealably engaging said rim.

29. A fluid conveying member according to claim 28 and characterized further in that said sealably engaging means includes means for frictionally engaging snugly said rim.

30. A fluid conveying member according to claim 29 and characterized further in that said rim and said frictionally engaging means respectively have mating tapered surfaces for engagement therebetween.

31. A fluid conveying member for use in a medical fluid flow system according to claim 27 and characterized further in that said stored closure means comprises a cap, said engagement means thereof including a screw thread means formed internally of said cap and a projecting male engaging portion extending interiorly within said cap, said blind closure-receiving means being adapted to sealably enclose the interior of said cap upon engagement therewith.

32. A fluid conveying member for use in a mdical fluid flow system or the like comprising a tubular portion having a fluid-conveying passageway therethrough, said tubular portion having connection means at the ends of its said fluid-conveying passageway for engagement with other fluid conveying members in fluid communication therewith, at least one closure means of the type having engagement means formed for selective port-closing engagement with a medical stopcock valve assembly, and a closure storage member on said tubular portion, said closure storage member having at least one blind closure-receiving portion formed thereon out of operative communication with said fluid passageway and having a portion formed for engagement by a stored closure means having engagement means identical to said at least one closure means to receive and retain said stored closure means for storage thereof when not in port-closing use to prevent loss thereof and to provide ready access thereto for tube-closing use when desired, said closure storage member and said tubular portion having mated affixation means formed thereon for detachable receipt of said closure storage member on said tubular portion for ready access to said stored closure means for port closing use and for ready removal of said closure storage member from said tubular portion following use of said stored closure means for replenishment with other closure means or replacement by another closure storage member with other closure means stored thereon.

33. A fluid conveying member for use in a medical fluid flow system according to claim 32 and characterized further in that said stored closure means comprises a cap, said engagement means thereof including a projecting male engaging portion formed thereon for engagement in a mating female member, and said portion of said blind member is formed as a tubular female fitting adapted for mating receiving engagement with said projecting portion of said stored closure means.

34. A fluid conveying member for use in a medical fluid flow system according to claim 32 and characterized further in that said blind closure-receiving means is adapted for sealing said engagement means of said stored closure means for maintaining said engagement means sterile.

35. A fluid conveying member for use in a medical fluid flow system according to claim 34 and characterized further in that said stored closure means comprises a cap having an outer rim and having said engagement means formed interiorly, said blind closure-receiving member including means for sealably engaging said rim.

36. A fluid conveying member for use in a medical fluid flow system according to claim 35 and characterized further in that said sealably engaging means includes means for frictionally engaging snugly said rim.

37. A fluid conveying member for use in a medical fluid flow system according to claim 34 and characterized further in that said stored closure means comprises a cap, said engagement means thereof including screw thread means formed internally of said cap and a projecting male engaging portion extending interiorly within said cap, said blind closure-receiving means being adapted to sealably enclose the interior of said cap upon engagement therewith.

* * * * *

UNITED STATES PATENT OFFICE
CERTIFICATE OF CORRECTION

Patent No. 4,566,480   Dated January 28, 1986

Inventor(s) Allan M. Parham

It is certified that error appears in the above-identified patent and that said Letters Patent are hereby corrected as shown below:

Column 6, Line 38, delete "tubulr" and insert therefor — tubular —.

Column 9, Line 55, delete "selctive" and insert therefor — selective —.

Column 11, Line 57, delete "mdical" and insert therefor — medical —.

Column 13, Line 26, delete "mdical" and insert therefor — medical —.

*Signed and Sealed this*

*Twenty-third* Day of *September 1986*

[SEAL]

*Attest:*

DONALD J. QUIGG

*Attesting Officer*    *Commissioner of Patents and Trademarks*